(12) United States Patent
Sobota et al.

(10) Patent No.: US 6,249,706 B1
(45) Date of Patent: Jun. 19, 2001

(54) ELECTROTHERAPY SYSTEM

(76) Inventors: John Sobota, 89 Blackburn Drive W., Edmonton, Alberta (CA), T6W 1B1; Gerald Zagrosh, #22, 9703 174th Street, Edmonton, Alberta (CA), T5T 6C5

( * ) Notice: Subject to any disclaimer, the term of this patent is extended or adjusted under 35 U.S.C. 154(b) by 0 days.

(21) Appl. No.: 08/943,770

(22) Filed: Oct. 6, 1997

Related U.S. Application Data

(63) Continuation-in-part of application No. 08/618,264, filed on Mar. 18, 1996, now abandoned.

(51) Int. Cl.$^7$ .................................................. A61N 1/00
(52) U.S. Cl. ............................. 607/115; 607/2; 607/63; 606/41
(58) Field of Search ......................... 607/75, 76, 72, 607/59, 64, 145, 150, 151, 115, 2, 50, 51, 62, 63; 606/41, 42

(56) References Cited

U.S. PATENT DOCUMENTS

| | | | |
|---|---|---|---|
| 4,232,680 | * 11/1980 | Hudleson et al. | 607/46 |
| 4,582,063 | * 4/1986 | Mickiewicz et al. | 607/72 |
| 4,622,973 | * 11/1986 | Agarwala | 607/72 |
| 4,841,973 | * 6/1989 | Stecker | 607/72 |
| 5,131,389 | * 7/1992 | Giordani | 607/76 |
| 5,470,349 | * 11/1995 | Kleditsch et al. | 607/75 |
| 5,620,483 | * 4/1997 | Minogue | 607/145 |

* cited by examiner

Primary Examiner—Linda C. M. Dvorak
Assistant Examiner—R. Kearney
(74) Attorney, Agent, or Firm—Alan J. Atkinson

(57) ABSTRACT

An apparatus for applying electrical current to biological tissue such as skin, bone or muscle. A portable housing can be powered with a battery or attached cord leading to an alternating current or direct current power supply. An extendible arm permits a person to apply the treatment without assistance, and the housing can be operated with a single hand. An amplifier generates a high voltage direct current, and a controller generates a high quality square waveform output. Such waveform comprises an output to an electrode assembly in electrical contact with the biological tissue. The electrode assembly comprises at least one negative electrode and at least one positive electrode which generate an electric current through the biological tissue between the positive and negative electrodes. The electrode assembly is movable relative to the biological tissue so that the current path is continually changing. The electrode assembly can comprise a plurality of negative and positive electrodes to create multiple current paths through the biological tissue. The controller can selectively modify output signal functions such as the amplitude, pulse rate, pulse sweep, frequency, and frequency sweep rate to provide different electrical currents to the biological tissue during operation. A display engaged with the controller indicates the output signal functions and provides controls for selectively modifying the output signal function.

28 Claims, 6 Drawing Sheets

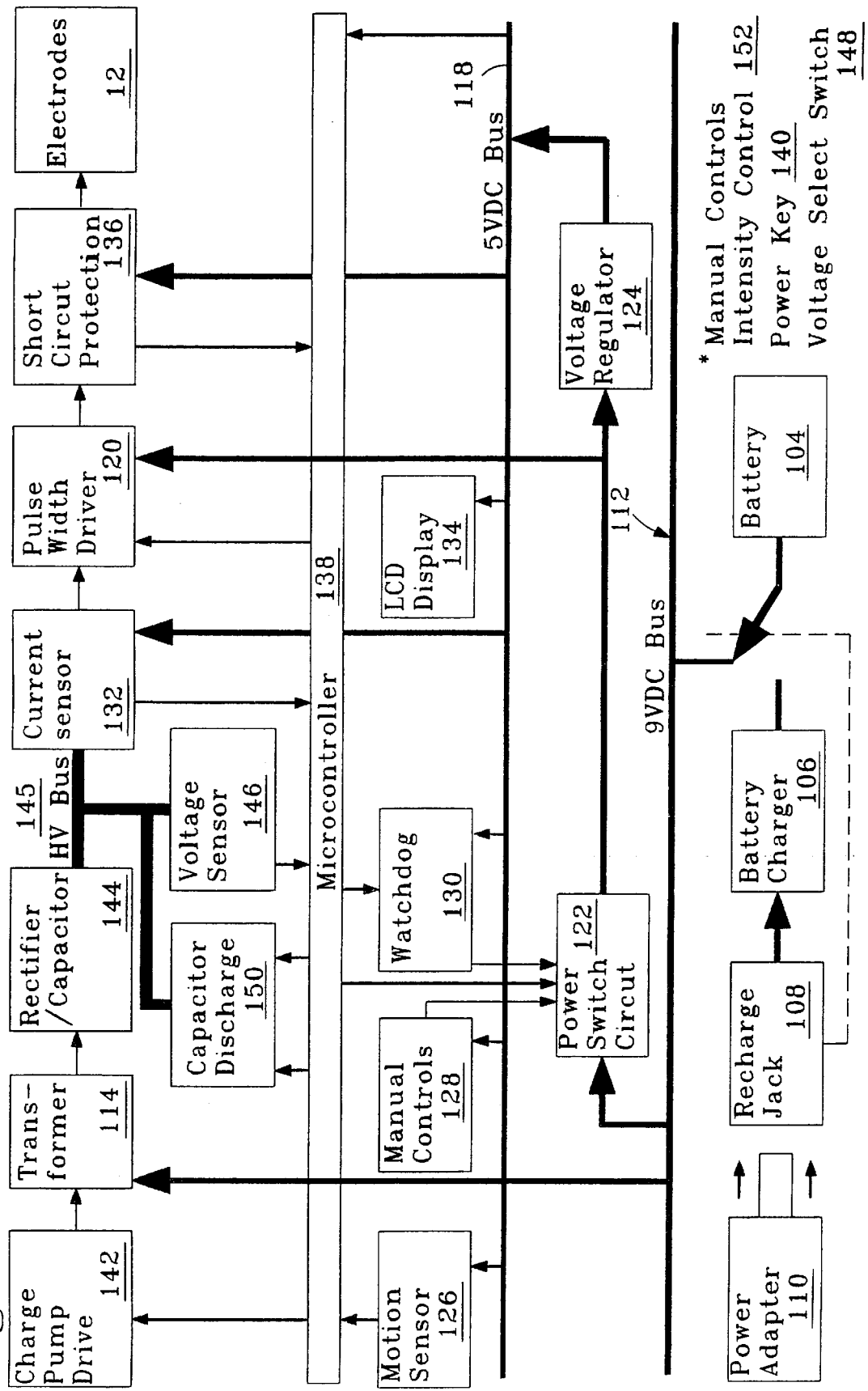

ELECTROTHERAPY SYSTEM

This Application is a continuation-in-part patent application of U.S. Ser. No. 08/618,264 filed Mar. 18, 1996 now abandonded, by Sobota et al. and entitled "Electrotherapy System."

BACKGROUND OF THE INVENTION

The present invention relates to the field of therapeutic technology for healing biological tissue with electricity. More particularly, the present invention relates to an improved electrotherapy system for applying electrical microcurrents to biological tissue such as a person's body.

Electricity promotes healing of biological tissue damage and provides an anesthetic to pain. This result is believed to be related to the properties and characteristics of biological cells. Biological cells contain a bioelectrical potential across the stable cell membrane. The cells can be stimulated by a nerve signal or external stimulus which disrupts the ionic balance in the cell. Additionally, the polarity of a cell can be reversed in different states of rest or activity. One form of biological cell damage hinders the cell ability to return to an equilibrium condition. Electrical treatments are believed to stimulate biological cells to emulate or to regain normal cell function.

Electrical treatments have been attempted to treat arthritis, biological tissue damage, nerve damage, calcification and other ailments. Prior art devices have utilized different frequencies, pulse rates, amplitudes, and magnetic fields in the search for therapeutic and anesthetic treatments. Although alternating current electrical fields have been applied to tissue, alternating currents can cause undesirable electrolysis at the contact point between an electrode and the tissue.

Square waveform electrical currents are known to be effective for promoting healing and curative effects. Consequently, efforts have been made to create square waveforms for application to biological tissue. However, such efforts have not produced a satisfactory device for generating pure waveforms at high voltage. Representative examples of prior art devices, including devices having positive and negative electrodes attached to a person's body, are described in the following references.

In U.S. Pat. No. 4,554,923 to Batters (1985), an electrically conductive glove was placed on a person's hand. Electric current was passed through the glove and hand to reduce pain and edema in the person's joints. The glove permitted an electrode to be stationary relative to the hand and facilitated electrical contact between the glove and hand without an external conductive medium.

In U.S. Pat. No. 4,509,521 to Barry (1985), headache pain was treated by applying an electrode to a person's neck or head, and by attaching a single ground electrode to a distal portion of the person's body. Electrical pulses from the electrode were applied between 60 and 150 volts and with a pulse width between 35 and 45 microseconds. The patent opined that each pulse should have the characteristics of a square waveform, and that other waveform shapes were not successful in providing relief. However, the disclosed device utilized a 20 turn primary and a 200 turn secondary transformer for altering the input to output voltage after the waveform was created. This device has inherent limitations because internal resistances in the transformer break down the waveform quality and prevent the formation of a square waveform.

U.S. Pat. No. 4,233,965 to Fairbanks (1980) described a device having two electrodes and a magnet for transmitting electricity through a person's body. One of the electrodes cooperated with a concentric electromagnet to produce a magnetic field for driving current into the tissue and toward a second electrode near the person's head. Rectangular or square wave positive polarity pulses were applied through a first electrode, and electrolysis at the tissue-electrode interface was minimized by the spreading effects of the magnetic field. Low voltage treatments between 20 and 27 volts DC at up to 400 microamps were applied continuously for up to eight hours.

U.S. Pat. No. 3,946,745 to Hsiang-Lai et al. (1976) described a device for generating an electrical signal comprising successive pulse pairs of opposite polarity, referred to as biopulses. Each biopulse included a fore-pulse and an aft-pulse having a reverse polarity. An electrode was attached to the tissue, and a signal pulse generator included a transformer for increasing the biopulse voltage. The output transformer generated an irregular waveform transmitted directly to the electrode load. To reduce the distortion of the output, a pair of resistors connected in parallel were substituted for the transformer so that open circuiting of a resistor would flow current through the other resistor. However, the patent disclosure anticipated that open circuiting of both resistors was possible, and that a potentially dangerous hazard might exist.

These electrical devices demonstrate the difficulty of generating a high voltage square waveform for application to biological tissue. Although transformers have been positioned between low voltage circuits and electrodes to step up the voltage after the waveform is generated, such waveforms are significantly distorted. High quality transformers reduce the amount of waveform distortion but are expensive and do not efficiently produce the desired microcurrent treatment. A need, therefore, exists for an improved system for providing electrical stimulation to a person's body.

SUMMARY OF THE INVENTION

The present invention provides an apparatus manipulable by a person for applying electrical current to biological tissue. The apparatus comprises a housing for movement proximate to the biological tissue, an amplifier engaged with a power supply for providing a high voltage signal, a controller for generating a square waveform output from said high voltage signal, and an electrode assembly engaged with the controller for electrical contact with the biological tissue. The electrode assembly comprises at least one negative electrode and at least one positive electrode for transmitting electric current through the biological tissue.

In other embodiments of the invention, an extendible arm permits the electrode assembly to be moved to a position distal from the housing. The controller can automatically change the square waveform output or can be manually operated to adjust various output parameters. Safety disconnects prevent improper or inappropriate contact between the electrode assembly and the biological tissue.

BRIEF DESCRIPTION OF THE DRAWINGS

FIG. 9 illustrates a schematic for one embodiment of the invention.

DESCRIPTION OF THE PREFERRED EMBODIMENTS

The present invention provides a unique apparatus for supplying microcurrent stimulation to biological tissue. As used herein, the term "biological tissue" includes skin, muscle, bone, nerves, tendons, and other parts of a biological organism such as a person or domestic animal. Although the invention is principally described herein for use with human patients or subjects, the invention is equally beneficial to livestock and other animals.

Figure 1:
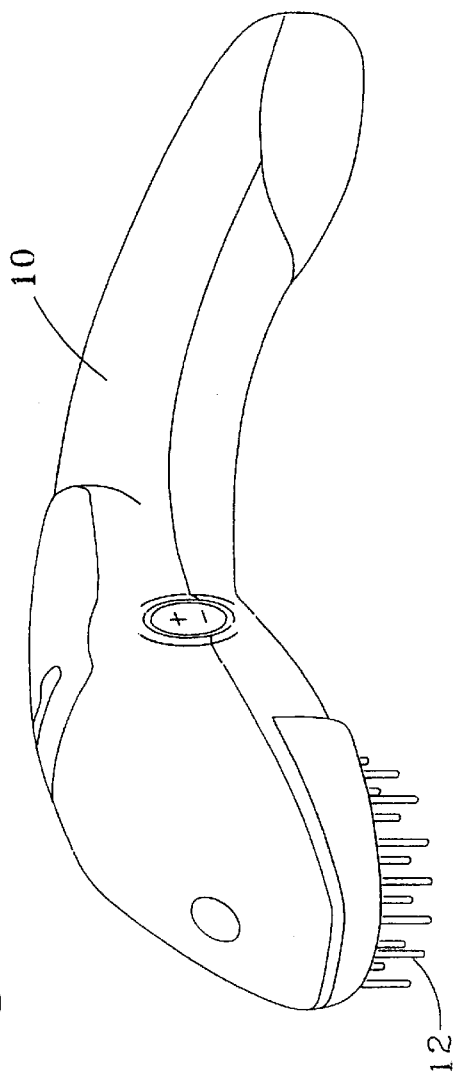
FIG. 1 illustrates an elevation view for one embodiment of the invention.

Referring to FIG. 1, an elevation view for one embodiment of the invention is illustrated. Housing 10 is constructed from an inorganic or organic material which can be formed in the desired shape. Housing 10 is preferably formed with a plastic, injected resin or other material that resists electrical conductivity. Housing 10 is formed with multiple sections as described below for facilitating assembly and operation of the apparatus. Electrode assembly 12 transfers electric microcurrents from the apparatus to the biological tissue of a person or other biological organism. In a preferred embodiment of the invention, electrode assembly 12 is placed in contact with a persons' skin as described below.

Figure 2:
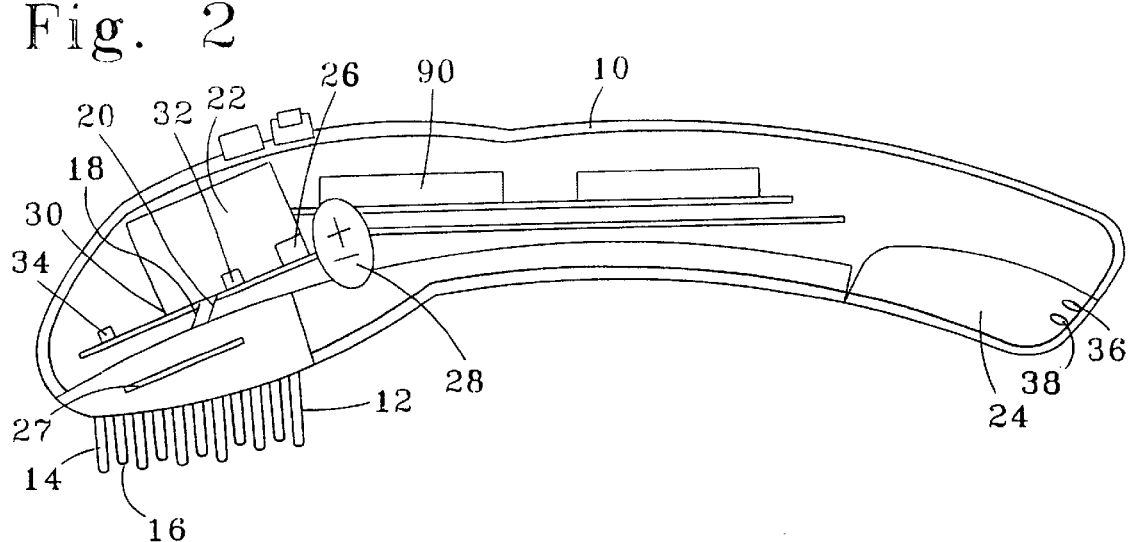
FIG. 2 illustrates a sectional view of the inventive embodiment in FIG. 1.

FIG. 2 illustrates a sectional view for one embodiment of the invention wherein electrode assembly 12 is formed with positive charge electrodes 14 and negative charge electrodes 16. Although a plurality of electrodes 14 and 16 are shown, various combinations and configurations of multiple or single positive charge electrode 14 and a single negative electrode 16 can be utilized to accomplish the functional result desired. Electrodes 14 and 16 can comprise machined pins having a continuously smooth end and are preferably formed with a noncorrosive material such as stainless steel, gold or nickel. Electrode assembly 12 is connected with electrically conductive wires 18 and 20 to controller 22, which in turn is engaged with battery 24 (conductors not shown). Amplifier 26 can boost the nine volt direct current ("VDC") of battery 24 to a high voltage between 50–500 VDC. Amplifier 26 is engaged with multi-position switch 27 which permits the user to select the desired voltage within a particular voltage range. Switch 27 can comprise a rheostat, multiposition electrical switch, or circuit suitable for permitting user control over the output voltage. This feature of the invention allows for compensation to the user's skin type, site humidity, and moistness of the user's skin.

Controller 22 includes manually operated switch 28 for selecting a waveform intensity to provide to amplifier 26. Controller 22 also includes multiple printed circuit boards such as printed circuit board ("PCB") 30 to provide a direct current square waveform output for transmission to electrode assembly 12 and other functions. Manual switch 28 can selectively permit or cease the transmission of the output to electrode assembly 12. PCB 30 can support components such as switching regulator 32. A sensor such as motion switch 34 can automatically switch off battery 24 if electrode assembly 12 is not moved relative to the biological tissue within a selected period of time.

Power supply or battery 24 provides power to controller 22 and electrode assembly 12. In one embodiment of the invention, battery 24 can comprise a nine volt battery contained within housing 10. In a preferred embodiment of the invention, battery 22 comprises a rechargable battery that can be recharged by attaching contacts 36 and 38 to a converter (not shown) communicating with an alternating current (AC) power source. In another embodiment of the invention, battery 24 can be replaced with another form of power supply such as a wire (not shown) attached to housing 10 for communicating direct current to controller 20. In another embodiment of the invention, the power supply can comprise a rectifier or electrical circuit for converting the alternating current to direct current.

Figure 3:
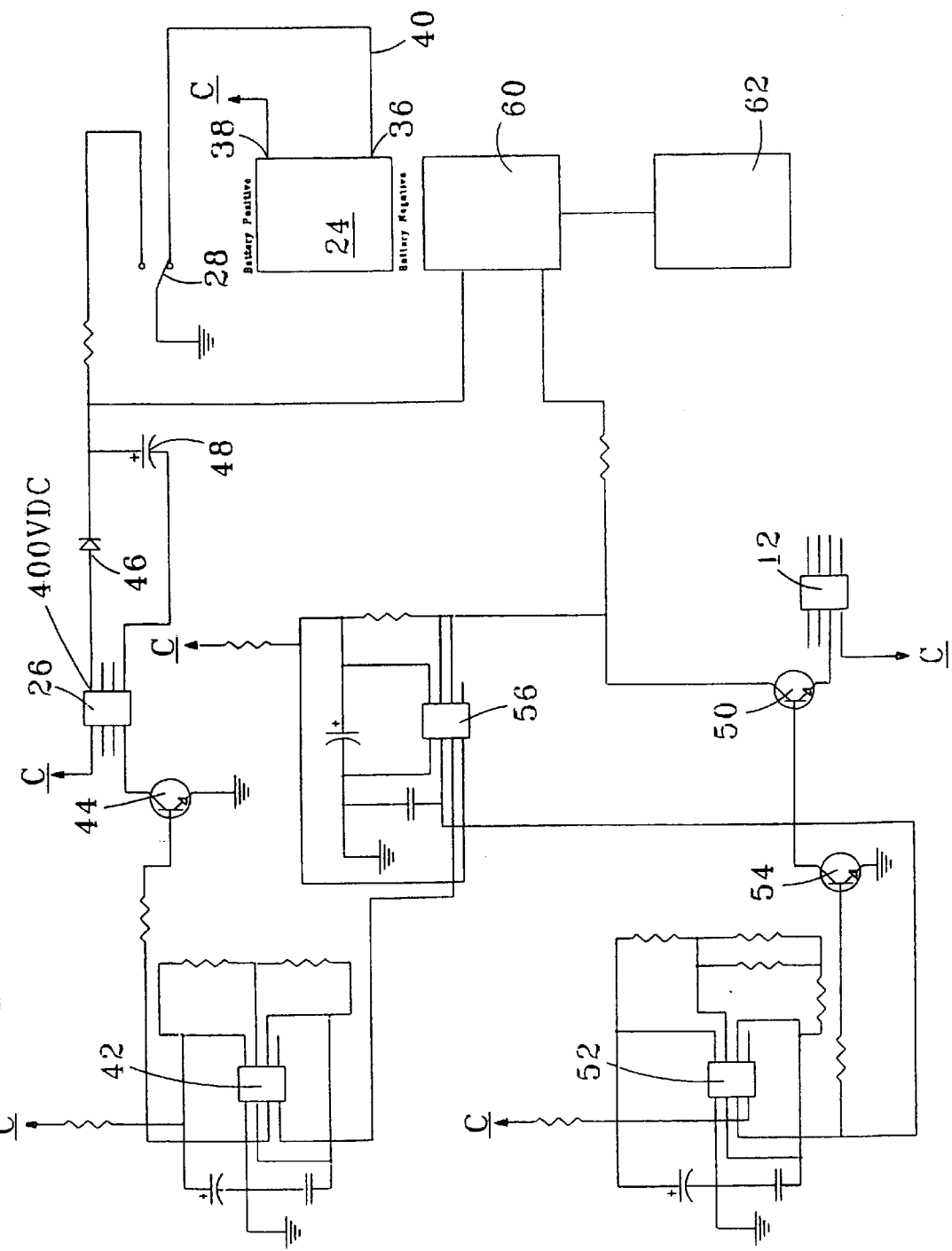
FIG. 3 illustrates one embodiment of a circuit utilizing the invention.

FIG. 3 illustrates a representative circuit for one embodiment of the invention. Battery 24 has negative terminal 36 engaged with lead wire 40 and has positive terminal 38 connected to common lead identified as "C". Manual switch 28 selectively opens or closes the conductivity path leading to negative terminal 36 to provide direct current power supply to the system. Amplifier 26 cooperates within the circuit and with microchip 42 and transistor 44 to step up the nine volt battery potential to a high voltage in a preferred range between 50 and 500 volts. Microchip 42 is engaged with common "C" and drives transistor 44 to pull large currents through amplifier 26. Transistor 44 can comprise a cascading transistor such as a Darlington Power Transistor which uses one internal transistor to boost the current for another internal transistor.

In the circuit illustrated in FIG. 3, the output voltage from amplifier 26 is shown at 400 volts direct current ("VDC"). Diode 46 rectifies and smooths the current from the high voltage side of amplifier 26. Capacitor 48 is charged at a voltage of 400 VDC, and current is selectively transmitted as output signal to negative charge electrode 16 with Field Effect Transistor ("FET") 50. The switching of FET 50 is controlled with microchip 52, which provides a timer function to FET 50 through transistor 54. Microchip 52 controls the pulses of the output signal. In one embodiment of the invention, microchip 52 can drive FET 50 at 320 VDC, between 5–100 microseconds pulse duration, ten times per second. Microchip 52 can provide a potentiometer function wherein the width and rate of such functions is modified.

FET 50 is engaged with electrode assembly 12, and specifically with negative charge electrode or electrodes 16. The output signal delivered by FET 50 to negative charge electrodes 16 comprises an extremely high quality square waveform at 400 VDC. This result is significantly more effective than prior art techniques which created a waveform at low voltage, and then stepped-up the voltage with a transformer. This enhancement occurs because the quality of transformers significantly increases the cost, and because transformers have internal resistances which degrade the purity of the resulting waveform. By creating a square waveform shape at the final voltage of 400 VDC, a pure waveform output is delivered from FET 50 to electrode assembly 12.

The circuit illustrated in FIG. 3 shows only one possible construction of the invention, wherein a high voltage signal is cleanly switched to generate a relatively pure square waveform from the output signal to electrode assembly 12. It will be appreciated that other circuits and devices performing the equivalent function are contemplated within the scope of the invention. Representative examples of such circuits and devices include switching power regulators or voltage multiplier circuits comprised of diodes and capacitors which convert an alternating current signal to a high voltage direct current output.

Microchip 56 can comprise a power saving device which selectively opens the circuit to battery 24 when capacitor 48 is fully charged, thereby avoiding power losses from battery 22 during the time after capacitor 48 is fully charged and before capacitor 48 is discharged.

Microprocessor 60 can be engaged with the circuit shown in FIG. 2 to control numerous functions related to the output signal amplitude, pulse rate, and pulse magnitude. For example, microprocessor 60 can "sweep" the pulse rate or frequency across selected ranges. Microprocessor 60 can control the pulse width, the width sweep period, the width sweep depth, the frequency, the frequency sweep depth, and the frequency sweep period. Additionally, microprocessor 60 can control other functions such as switches, sound effects and sensation feedback sensors or monitors. All of these functions can be indicated on display 62 engaged with microprocessor 60. Although microprocessor 60 simplifies the operation of these various functions, it will be appreciated that other circuits and devices can perform the same functions within the scope of the invention.

Figure 4:
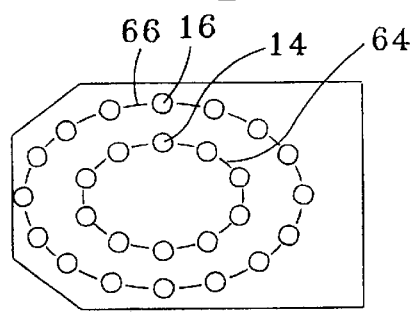
FIG. 4 illustrates one embodiment of an electrode pattern.
Figure 5:
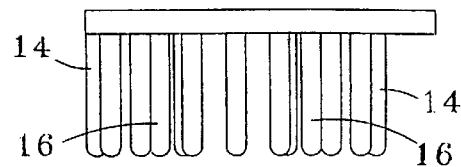
FIG. 5 illustrates a side view of the electrode pattern in FIG. 4.

Referring to FIG. 4, one embodiment of electrode assembly 12 is illustrated wherein a plurality of negative charge electrodes 16 are positioned within an interior array 64, along the broken line illustrated, and a plurality of positive charge electrodes 14 are positioned within an exterior array 66 along the broken line illustrated. As shown in FIG. 4, the interior and exterior arrays 64 and 66 substantially form concentric ellipses wherein each negative charge electrode 16 is proximate to at least two positive charge electrodes 14. This configuration creates multiple microcurrent paths at different vector angles for each negative charge electrode 16, thereby increasing the microcurrent path coverage for each negative charge electrode 16. FIG. 5 illustrates a side view of electrode assembly 12.

Regardless of which direction electrode assembly 12 is moved relative to the biological tissue of a subject, the microcurrent between a negative charge electrode 16 and one positive charge electrode 14 will sweep across the biological tissue in a path which complements the path covered by the microcurrent with the other paired positive charge electrode 14, thereby enhancing the surface coverage of the microcurrents. While the sweeping effect of one positive charge electrode 14 and one negative charge electrode 16 can accomplish surface coverage, such coverage is more complete and provides greater redundancy if a plurality of electrodes are incorporated within electrode assembly 12. Different electrode configurations can accomplish a functional equivalent result without departing from the scope of the invention.

Figure 6:
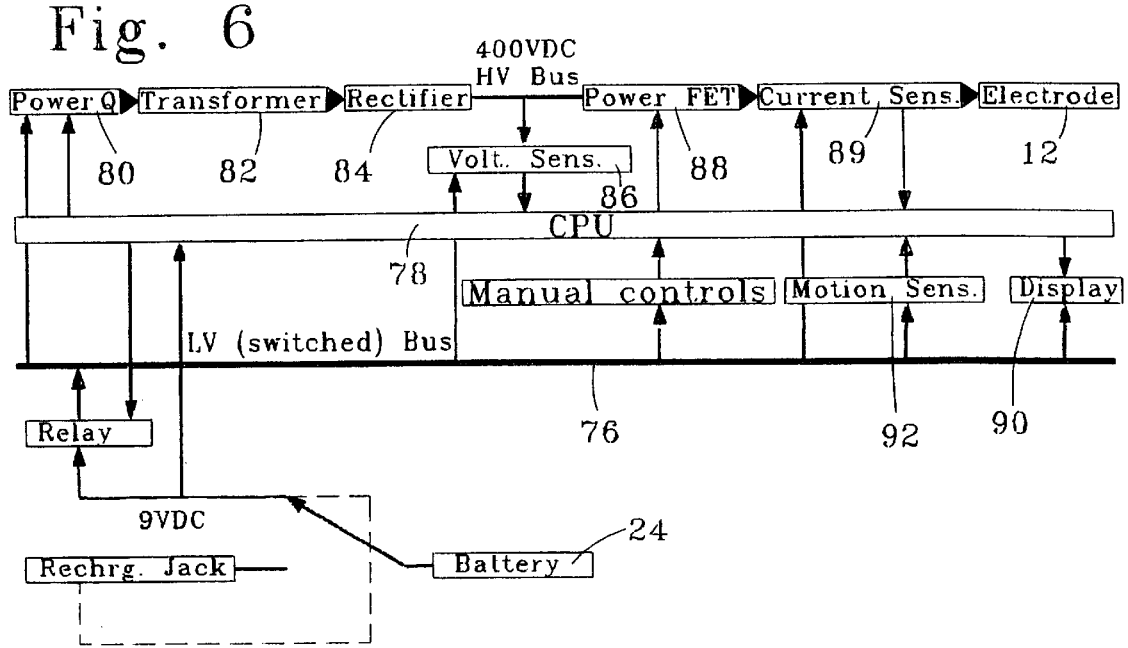
FIG. 6 illustrates an alternative embodiment of a circuit incorporating the present invention.

FIG. 6 illustrates a schematic circuit representative of one embodiment of the invention. As shown, battery 24 is connected to low voltage bus 76 to power microprocessor 78, power transistor 80 and amplifier or transformer 82. The nine volt battery potential is stepped-up to 400 VDC and is smoothed with rectifier/capacitor 84. Any fluctuations in such high output voltage are detected with voltage sensor 86 for transmission to microprocessor 78. If the high voltage drops below a selected threshold level, microprocessor 78 runs transistor 80, switching at 30 kHz and injecting energy into transformer 82, thereby causing rectifier/capacitor 84 to charge up the internal capacitor described above to the selected voltage.

Microprocessor 78 selectively controls FET 88 for generating a high quality square waveform output transmitted to electrode assembly 12 as the square waveform output signal. Current sensor 89 is positioned between FET 88 and electrode assembly 12 to monitor current pulses transmitted to electrode assembly 12 and to transmit a signal to microprocessor 78 indicating such current pulses. Signals indicating such data can be transmitted to display 90 on the low voltage side of microprocessor 78, and can permit microprocessor 78 to monitor and control current pulses emitted by electrode assembly 12.

Motion sensor 92 can be engaged between low voltage bus 76 and microprocessor 78 to monitor movement of electrode assembly 12 attached to housing 10. Motion sensor 92 generates a signal to microprocessor 78 if electrode assembly 12 is not moved for a selected interval of time, and microprocessor 78 can be programmed to cease all electric power transmitted to FET 88 and to electrode assembly 12. This power disconnect creates a power switch which prevents electrode assembly 12 from continuously providing electrode current to the same segment of biological tissue, and provides a power conservation feature for preventing power drains from battery 24 when electrode assembly 12 is not in use.

Figure 7:
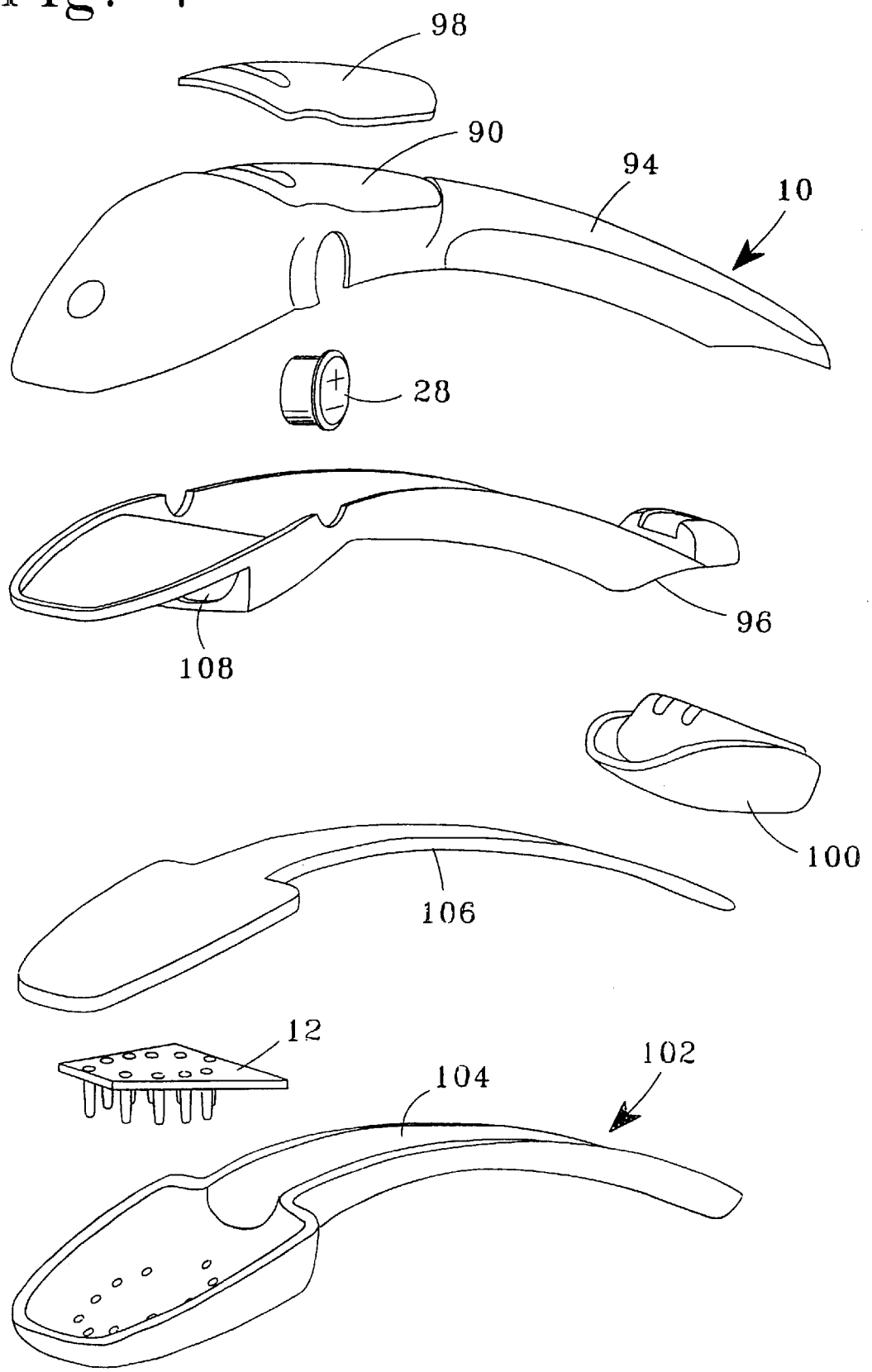
FIG. 7 illustrates an exploded view for one inventive embodiment.

FIG. 7 illustrates an exploded view for one embodiment of the invention which shows major components of the apparatus. Housing 10 is generally formed with upper section 94 and lower section 96. Display cover 98 is proximate to display 90 and can comprise a transparent lens for viewing display 90. Battery clip 100 is attachable to lower section 96 to permit replacement of battery 24. Switch 28 is positioned between upper section 94 and lower section 96.

Figure 8:
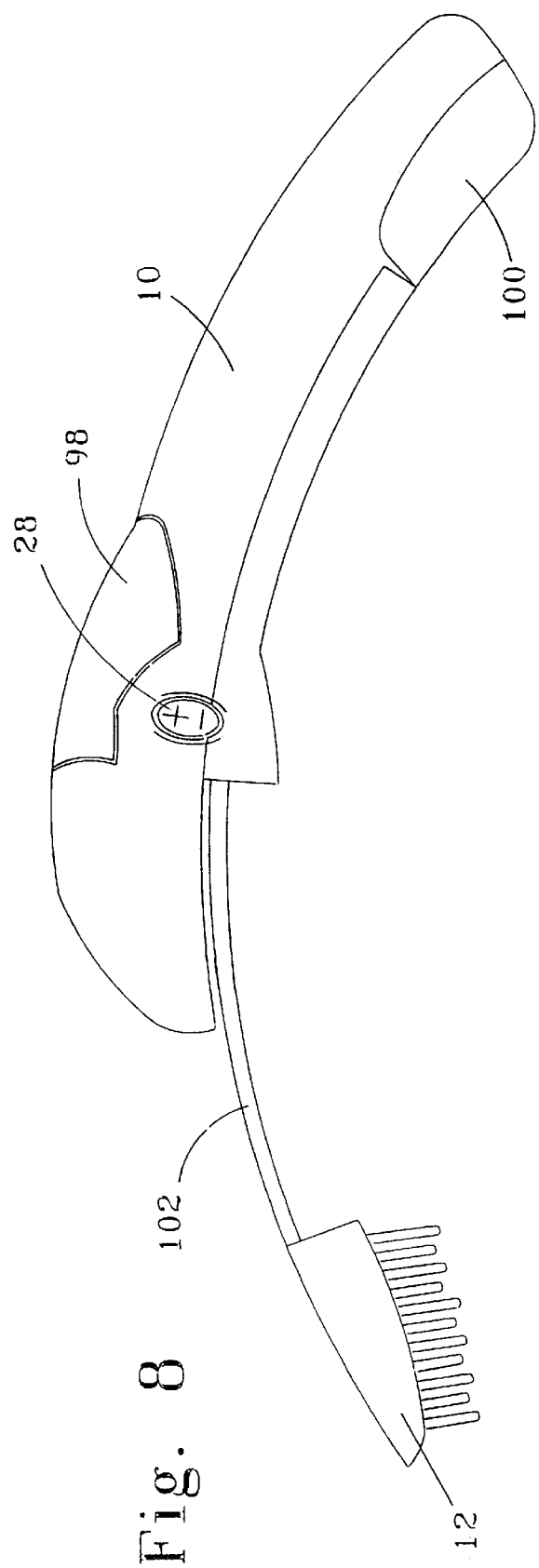
FIG. 8 illustrates an inventive embodiment having an extendible reach.

Electrode assembly 12 is positioned within extendible arm 102, formed with lower arm section 104 and upper arm section 106. Extendible arm 102 is longitudinally moveable within aperture 108 through lower section 96. Extendible arm 102 is initially positioned in a retracted position as shown in FIG. 1, and is movably extendible into a fully extended position as shown in FIG. 8. A release mechanism (not shown) can selectively retain or release extendible arm 102 from fixed engagement relative to housing 10. As shown in FIG. 8, extendible arm 102 moves electrode assembly 12 to a position distal from housing 10, thereby increasing the reach and maneuverability. Although extendible arm 102 is shown in the fully retracted and extended positions, various intermediate positions between these limits can be accomplished with a suitable latch mechanism (not shown). Extendible arm 102 can comprise a single element, a telescoping arrangement or elements, or other structural shape sufficient to move electrode assembly 12 relative to housing 10. Extendible arm 102 uniquely permits a person to operate the apparatus without assistance, and to reach areas of the person's body inaccessible by other hand operated electrical devices. For example, extendible arm 102 permits a person to reach the middle of the person's back with electrode assembly 12, thereby enhancing the utility and effectiveness of the apparatus.

The invention permits a person to operate the apparatus with either hand, thereby permitting a person to treat all portions of the person's skin without assistance from another. The invention only requires one hand for operation, and does not require the active, simultaneous use of both hands. Extendible arm 102 permits unique flexibility in reach and coverage, without depending on attached cords or power lines attached to a remote power source.

FIG. 9 illustrates a schematic diagram for another embodiment of the invention. Electric power to the system can be provided through rechargable battery 104, which can comprise a nine volt nickel cadmium or nickel metal hydride battery. Battery charge circuit 106 is connected to recharger jack 108, which in turn can be connected to power adapter 110. When power adapter 110 is connected to a conventional AC power supply, battery 104 is disengaged from nine volt power bus 112. This feature of the invention prevents use of the electrotherapy system and electrode assembly 12 while battery 104 is being recharged, thereby providing a built-in safety feature which prevents inadvertent operation when the system is connected to a AC power supply. Alternatively, battery 104 could comprise a nonrechargeable alkaline nine volt battery engaged with the system at all times and replaced when the stored battery power is dissipated.

When power adapter 110 is not plugged into recharger jack 108, battery 104 is engaged with nine volt power bus 112. This engagement permits operation of the various functions of the system. By selectively engaging battery 104 with battery charge circuit 106 or nine volt power bus 112 as illustrated, recharger jack 108 provides a reliable, internal switching mechanism which does not depend on a power system for operation. Instead, such switching function depends only on the presence or absence of a connection between power adapter 110 and recharger jack 108.

As shown in FIG. 9, nine volt power bus 112 is engaged with different functional operating systems. In this embodiment of the invention, certain operating systems require regulated DC power and other operating systems require unregulated DC power. For example, nine volt power bus 112 provides unregulated DC power to transformer 114 and to pulse width driver 116. Transformer 114 draws significant power supply current in sharp pulses and is connected to nine volt power bus 112 instead of five volt bus 118. Although certain voltage noise will be created by nine volt power bus 112, transformer 114 does not require connection to a switched power supply because transformer 114 does not use energy when signals are not being sent to transformer 114.

Alternatively, pulse width driver 120 requires regulated DC power and is connected to power switch circuit 122 for this purpose. Power switch circuit 122 is powered by nine volt power bus 112 and is connected to voltage regulator 124. Pulse width driver 120 is connected to power switch circuit 122 so that pulse width driver 120 is automatically powered-down when the entire operating system is powered-down.

Voltage regulator 124 receives its power source from the nine volt source provided at the output of power switch circuit 122. Voltage regulator 124 is engaged with five volt bus 118, which in turn is engaged with functional blocks such as motion sensor 126, manual controls 128, watchdog 130, current sensor 132, LCD display 134, short circuit protection module 136, and microcontroller 138. The operation of each functional block is described below. Voltage regulator 124 protects such functional blocks by controlling power to the clean, regulated five volt DC bus 118, and provides a suitable power source for the operation of sensitive electronic blocks such as microcontroller 138 which require an unwavering, stable voltage.

Microcontroller 138 controls power switch circuit 122 when microcontroller 138 is powered-up and further has a direct control connection to manual controls 128. Controls 128 include a subfunction power key 140, and direct control connection is required so that power key 140 can start the system from a powered-down state when microcontroller 138 is powered-down and is unable to perform a control function. If power key 140 is activated while the system is powered-up, microcontroller 138 will interpret this event as an operator command to turn the system off. In this event, microcontroller 138 sends a signal to power switch circuit 122 to power-down the system.

Pulse width driver 120 is directly engaged with nine volt power bus 112 through the output from power switch circuit 122. Because pulse width driver 120 does not draw a significant amount of power, problematic noise is not generated. Pulse width driver 120 is connected to nine volt power bus 112 instead of five volt bus 118 because pulse width driver 120 requires a higher voltage than five volts. By connecting pulse width driver 120 to the output of power switch circuit 122, pulse width driver 120 is powered-down when the system is turned off.

The electricity delivered to electrode assembly 12 uniquely comprises a high voltage DC source formed by "carving out" a square waveform from the high voltage source. Microcontroller 138 orchestrates this function by delivering a square waveform to charge pump driver 142 at a frequency optimized for the most efficient power transfer within transformer 114. Charge pump driver 142 creates a waveform of the same frequency out of nine volt source supply from nine volt power bus 112 and provides such input to the primary winding of transformer 114. The secondary winding within transformer 114 is engaged with rectifier/capacitor 144 which converts the AC output to a high voltage DC level shown at HV Bus 145.

Voltage sensor 146 provides feedback to microcontroller 138 by providing the present voltage level at HV Bus 145. Microcontroller 138 continually compares such feedback voltage with the set voltage defined by the position of voltage select switch 148 located within manual controls 128. As previously described, voltage select switch 148 can comprise a four position switch having representative settings at 320 VDC, 280 VDC, 250 VDC, and 210 VDC. Other combinations of intensity positions can be selected to accomplish the function of providing maximum user control.

If the HV Bus 145 voltage detected by voltage sensor 146 is less than that defined by voltage select switch 148, then microcontroller 138 continues to send the square waveform to charge pump driver 142. Once microcontroller 138 determines that HV Bus 145 voltage has reached a selected value, microcontroller 138 ceases to send the square waveform to charge pump driver 142 until the voltage again falls below the setting. If microcontroller 138 senses through voltage sensor 146 that HV Bus 145 voltage is higher than the desired voltage as defined by the position of voltage select switch 148, microcontroller 138 operates capacitor discharge 150 to drain current from rectifier/capacitor 144.

Rectifier/capacitor 144 operates as an energy storage for HV Bus 145, and current can be drained from rectifier/capacitor 144 until the HV Bus 145 voltage is aligned with the selected voltage setting. This feature of the invention may be required when the operator changes voltage select switch 148 from a high setting to a lower setting. In this embodiment of the invention, microcontroller 138 regulates the HV Bus 145 voltage to the selected level at all times.

Microcontroller 138 controls a novel, very clean square voltage waveform not known in previous electrotherapy systems. The electrotherapy waveform is "carved out" of a high voltage DC supply supplied by HV Bus 145. Microcontroller 138 creates the square voltage waveform and maintains a consistent output frequency and pulse width (pulse duration) consistent with the operator selection.

On power-up, microcontroller 138 sets the pulse width to a minimum value. As microcontroller 138 receives instructions from intensity control 152 of manual controls 128, microcotroller 138 will increase or decrease the pulse width between this minimum level (5 microseconds) and a maximum level (100 microseconds). These are representative maximum and minimum durations during each waveform period when the HV bus is connected through to electrode assembly 12 by pulse width driver 120. Microcontroller 138 indicates the current intensity setting to the operator by displaying this information numerically as well as graphically on LCD display 134.

Capacitor discharge 150 will operate if five VDC bus 118 is powered-down for any reason. This includes a selected microcontroller 138 initiated power-down as well as power losses caused by a problem condition. When a power-down of five VDC bus 118 occurs, capacitor discharge 150 promptly drains rectifier/capacitor 144 down to zero volts.

Microcontroller 138 continually monitors several safety systems so that selected corrective action can be taken. Motion sensor 126 provides microcontroller 138 with information about the motion of electrode assembly 12 relative to the surface of a person's skin. If the user fails to move electrode assembly 12 on the skin for a predetermined period "A", microcontroller 138 will cease sending pulses to pulse width driver 120. If motion is resumed prior to predetermined time "B", microcontroller 138 will resume sending pulses at the original intensity. If the user fails to move electrode assembly 138 on the skin for the predetermined period "B", microcontroller 138 will execute a full power-down of the system.

Time periods "B" are greater than "A" because all times start from the beginning of the non-movement event, and working values for each are in the order of three seconds for "A" and one minute for "B".

Microcontroller 138 also monitors current sensor 132 as shown in FIG. 9. If the instantaneous current flowing from HV Bus 112 through current sensor 132 should exceed a predetermined amount such as one milliamp, microcontroller 138 initiates a full system power-down. This protects a user who has unusually low skin resistance from receiving excessive current into the body. This may be the case if electrode assembly 12 is applied to an open wound or to overly wet skin.

Microcontroller 138 also monitors a short circuit protection module 136 which is designed to detect a short circuit in the output states of the electrotherapy system. This condition may occur if pulse width driver 120 fails, or if the user applies electrode assembly 12 to a metal surface such as a watch or ring. Microcontroller 138, using information from short circuit protection module 136, can execute a full system power-down within five microseconds of the short circuit event. Sucb an event would also trigger the circuitry for current sensor 132, however short circuit protection module 136 can be designed to detect an event and to take action responsive to such event with maximum response to avoid internal component damage and to provide maximum protection to the user.

Watchdog 130 continually monitors the activity of microcontroller 138. If watchdog 130 determines that microcontroller 138 has failed, watchdog 130 immediately activates capacitor discharge module 150 to drain HV Bus capacitor 144. Subsequently, watchdog 130 executes a full power-down using power switch circuit 122. This safety feature is important because many of the other safety features depend on microcontroller 138 for operation.

Microprocessor 138 also continuously performs an "output check" of the signal being sent to electrode assembly 12. This safety feature consists of checking that a high voltage pulse is present when microprocessor 138 has instructed pulse width driver 120 to create a pulse, and that such pulse is absent when microprocessor 138 has not instructed pulse width driver 120 to create a pulse. If this output check fails, microprocessor 138 executes a full system power-down.

Figure 10:
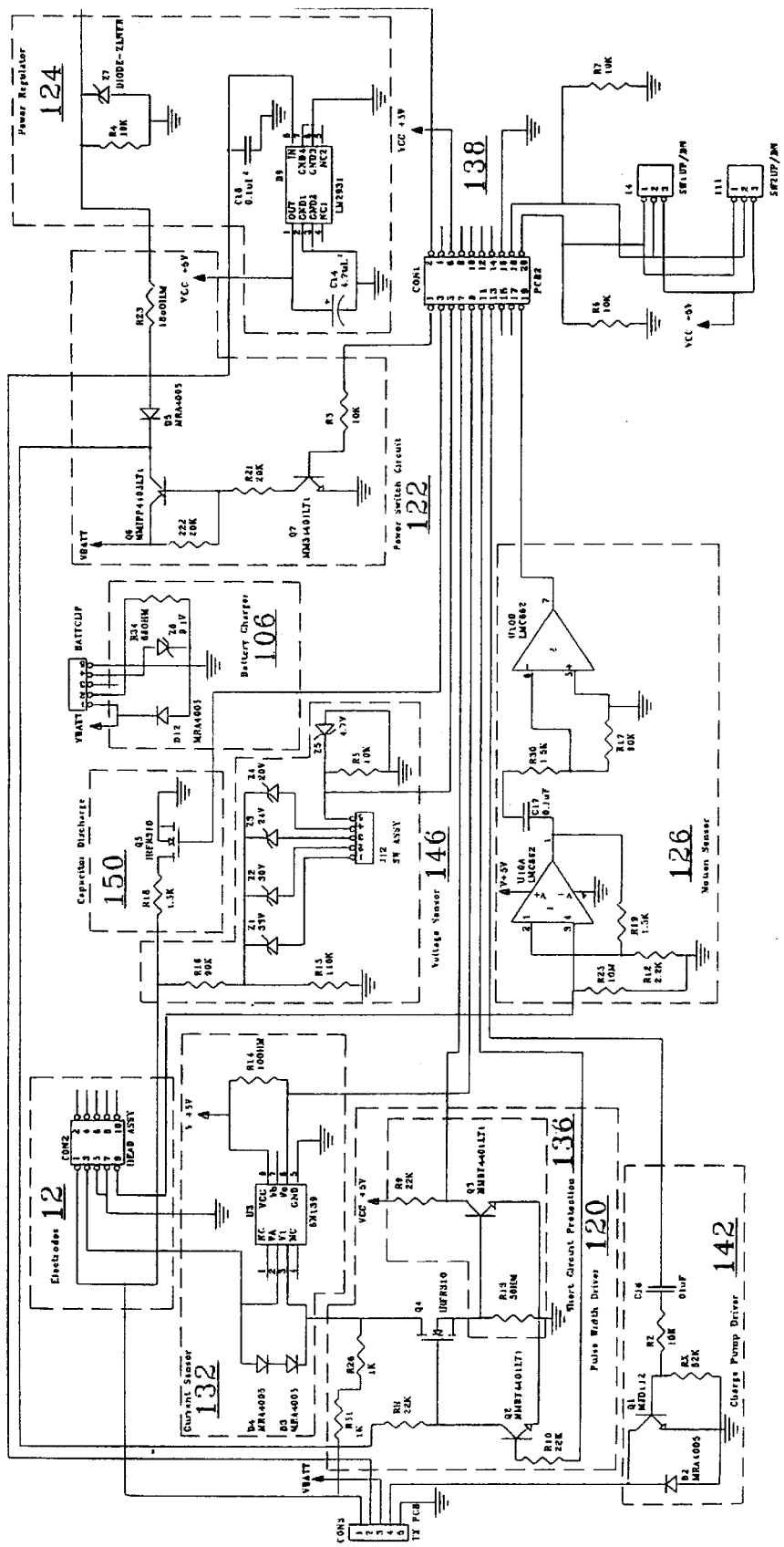
FIG. 10 illustrates a circuit diagram for certain functions illustrated in FIG. 9.

FIG. 10 illustrates a representative circuit for the inventive embodiment illustrated in FIG. 9. Such circuit illustrates functional characteristics of the inventive embodiment, and can be modified to accomplish the same or different functional results with different configurations.

In operation, housing 10 is manipulated so that electrode assembly 12 is continually moved over the biological tissue such as the subject's skin. Housing 10 is selectively sized and is sufficiently manipulable to permit operation of housing 10 with either of the person's hands. Continual movement of electrode assembly 12 restricts electric current "channeling" through low resistance paths in the subject by continually changing the location of positive charge electrodes 14 and negative charge electrodes 16. Distribution of electric microcurrents is spread to maximize the benefits of the system, and overexposure to low resistance paths within the subject is restricted.

By regulating continual movement of electrode assembly 12, the system significantly enhances the healing and curative effectiveness of the apparatus. Prior art techniques having fixed electrodes transmit electric current through the paths of least resistance, potentially missing certain areas of desired treatment. Conversely, the present invention provides a sweeping movement which continually changes the relative position of positive charge electrodes 14 relative to negative charge electrodes 16, thereby changing the current paths through the subject. This movement transmits electric current through the subject in a substantially uniform, flux-like manner.

By operating the parameters of display 90, the current transmitted through electrode assembly 12 can be increased or decreased while electrode assembly 12 is in contact with the biological tissue. This unique feature of the invention permits adjustment of the treating current as the apparatus is operated. Consequently, treatment does not necessarily cease, and the applied current is contemporaneously adjusted to the tolerance level of the person undergoing treatment. This feature of the invention is particularly important for persons having higher or relatively lower discomfort sensitivity during electrical microcurrent treatment. If motion of electrode assembly 12 is ceased or does not meet a selected profile, motion detector 34 will automatically cease power transfer from battery 24, thereby reducing possible overexposure to the person's biological tissue.

The invention uniquely isolates sensitive electronic circuits such as microcontroller 138 from damaging high voltage sources, and provides a novel apparatus and method for carving a pure, square waveform from a high voltage source. This purity of the square waveform has not been previously accomplished, and provides significantly enhanced clinical results over existing electrotherapy treatment systems.

Although the invention has been described in terms of certain preferred embodiments, it will be apparent to those of ordinary skill in the art that modifications and improvements can be made to the inventive concepts herein without departing from the scope of the invention. The embodiments shown herein are merely illustrative of the inventive concepts and should not be interpreted as limiting the scope of the invention.

What is claimed is:

1. An apparatus engagable with a power supply and manipulable by a person to apply electricity to biological tissue, comprising:
   a housing for movement proximate to the biological tissue;
   an amplifier attachable to the power supply for generating a high voltage direct current;
   a controller having a switch engaged with said amplifier for receiving said high voltage direct current from said amplifier and for generating a square voltage wave output from said high voltage direct current; and
   an electrode assembly attached to said housing and engaged with said controller for electrical contact with the biological tissue and for transmitting said square voltage wave output to the biological tissue without further amplification of said square voltage wave output, when said electrode assembly is moved relative to the biological tissue, wherein said electrode assembly comprises at least one negative electrode and at least one positive electrode proximate to said negative electrode for transmitting electricity from said square voltage wave output through the biological tissue between said positive and negative electrodes.

2. An apparatus as recited in claim 1, wherein said electrode assembly comprises a plurality of negative electrodes and a plurality of positive electrodes.

3. An apparatus as recited in claim 1, wherein the power supply comprises a battery attached to said housing and said amplifier is engaged with a positive terminal of said battery.

4. An apparatus as recited in claim 1, further comprising an extendible arm attached to said electrode assembly and moveable relative to said housing to selectively move said electrode assembly to a position distal from said housing.

5. An apparatus as recited in claim 4, wherein said extendible arm is enclosed by said housing when said extendible arm is retracted.

6. An apparatus as recited in claim 1, wherein said controller is capable of monitoring said high voltage direct current and is further capable of generating signals to maintain said high voltage direct current at a selected level.

7. An apparatus as recited in claim 1, wherein said controller is capable of selectively modifying the waveform width of said output.

8. An apparatus as recited in claim 1, wherein said controller is capable of sweeping the frequency of said output through a selected frequency range.

9. An apparatus as recited in claim 1, wherein said controller is capable of sweeping the pulse frequency of said output through a selected range.

10. An apparatus as recited in claim 1, wherein said controller adjusts the pulse width of said output.

11. An apparatus as recited in claim 1, wherein said controller includes a microcontroller engaged with a pulse width driver for controlling the waveform width of said output.

12. An apparatus as recited in claim 11, further comprising a power switch circuit engaged between said power supply and said amplifier, wherein said power switch circuit is further engaged with said pulse width driver.

13. An apparatus as recited in claim 12, further comprising a voltage regulator engaged with said power switch circuit for supplying power to said microcontroller at a voltage less than that of said power supply voltage.

14. An apparatus as recited in claim 12, wherein said microcontroller is capable of operating said power switch circuit upon the occurrence of a selected event to cease power flow through said power switch circuit.

15. An apparatus manipulable by a person to apply electricity to biological tissue, comprising:
   a housing for movement proximate to the biological tissue;
   a direct current power supply attached to and movable with said housing;
   an amplifier engaged with said power supply for generating a high voltage direct output;
   an energy storage engaged with said amplifier for receiving said high voltage direct output;
   a controller having a switch engaged with said energy storage for generating a square voltage wave output from said high voltage direct current;
   a negative electrode engaged with said controller for transmitting said voltage wave output to the biological tissue; and
   a positive electrode engaged with said power supply and in electrical contact with the biological tissue for permitting electricity to flow through the biological tissue between said positive electrode and said negative electrode.

16. An apparatus as recited in claim 15, further comprising a plurality of positive electrodes and negative electrodes, wherein each positive electrode is located proximate to a negative electrode to create an electrode pair, and wherein said output generates an electric current between each electrode pair in a path through the biological tissue.

17. An apparatus as recited in claim 15, wherein two positive electrodes are located proximate to a negative electrode, and wherein said output generates two electric current paths through the biological tissue between each negative electrode and each proximate positive electrode.

18. An apparatus as recited in claim 15, wherein said controller is capable of modifying the voltage of said output signal.

19. An apparatus as recited in claim 18, wherein said controller is capable of modifying the voltage of said output signal while said negative electrodes and said positive electrodes are in contact with the biological tissue.

20. An apparatus as recited in claim 1, wherein said voltage square wave output comprises a direct current output.

21. An apparatus as recited in claim 20, wherein said voltage square wave output is unipolar.

22. An apparatus as recited in claim 1, wherein said voltage square wave output has no feedback, and wherein current is determined by the biological tissue impedance.

23. An apparatus as recited in claim 1, wherein the power supply is limited to positive charge.

24. An apparatus as recited in claim 1, wherein said electrode assembly provides positive charge only to the biological tissue.

25. An apparatus as recited in claim 1, wherein said amplifier generates a voltage greater than 300 volts.

26. An apparatus as recited in claim 1, wherein said controller is capable of maintaining a constant frequency for the square voltage wave output.

27. An apparatus as recited in claim 1, wherein said controller alternates the square voltage wave output between the peak voltage and zero voltage.

28. An apparatus as recited in claim 1, further comprising a display for indicating the pulse width of said square voltage wave output.

* * * * *